US010441637B2

(12) United States Patent
Huang

(10) Patent No.: US 10,441,637 B2
(45) Date of Patent: Oct. 15, 2019

(54) METHODS FOR STRUCTURAL DETERMINATION OF SELENIUM DERIVATIZED NUCLEIC ACID COMPLEXES

(71) Applicant: SeNA Research, Inc., Marietta, GA (US)

(72) Inventor: Zhen Huang, Marietta, GA (US)

(73) Assignee: SeNA Research, Inc., Marietta, GA (US)

( * ) Notice: Subject to any disclaimer, the term of this patent is extended or adjusted under 35 U.S.C. 154(b) by 337 days.

(21) Appl. No.: 15/038,242

(22) PCT Filed: Nov. 21, 2014

(86) PCT No.: PCT/US2014/066823
§ 371 (c)(1),
(2) Date: May 20, 2016

(87) PCT Pub. No.: WO2015/077566
PCT Pub. Date: May 28, 2015

(65) Prior Publication Data
US 2016/0279250 A1    Sep. 29, 2016

Related U.S. Application Data

(60) Provisional application No. 61/909,732, filed on Nov. 27, 2013, provisional application No. 61/907,284, filed on Nov. 21, 2013.

(51) Int. Cl.
| A61K 38/46 | (2006.01) |
| C07K 1/30 | (2006.01) |
| G01N 33/53 | (2006.01) |
| C12N 9/22 | (2006.01) |
| C12N 9/96 | (2006.01) |
| A61K 47/61 | (2017.01) |
| G16H 50/50 | (2018.01) |
| G06F 19/00 | (2018.01) |

(52) U.S. Cl.
CPC ............ *A61K 38/465* (2013.01); *A61K 47/61* (2017.08); *C07K 1/30* (2013.01); *C12N 9/22* (2013.01); *C12N 9/96* (2013.01); *C12Y 301/26004* (2013.01); *G01N 33/5308* (2013.01); *G06F 19/00* (2013.01); *G16H 50/50* (2018.01); *Y02A 90/26* (2018.01)

(58) Field of Classification Search
None
See application file for complete search history.

(56) References Cited

U.S. PATENT DOCUMENTS

2012/0065387 A1    3/2012  Huang

FOREIGN PATENT DOCUMENTS

WO          02044321          6/2002
WO     WO 2007/120657     * 10/2007

OTHER PUBLICATIONS

Freisz et al., "Binding of Aminoglycoside Antibiotics to the Duplex Form of the HIV-1 Genomic RNA Dimerization Initiation Site", Angew. Chem. Int. Ed. 2008, 47, 4110-4113. DOI: 10.1002/anie.200800726.*
E. Dodson, "Is It Jolly SAD?", Acta Cryst. D., CCP4 Study Weekend, 2003, D59, pp. 1958-1965.*
McPherson & Cudney, "Optimization of crystallization conditions for biological macromolecules", Acta Cryst. F. (Struc. Biol. Comm.) , 2014, F70, pp. 1445-1467. doi:10.1107/S2053230X14019670.*
Sergenov et al., "Structural basis for Diels-Alder ribozyme-catalyzed carbon-carbon bond formation", Nature Structural & Molecular Biology, Mar. 2005, vol. 12, No. 3, pp. 218-224.*
Cudney R. Protein Crystallization and Dumb Luck. The Rigaku Journal. 1999. vol. 16, No. 1, pp. 1-7.*
De Vivo, et al., "Phosphodiester cleavage in ribonuclease H occurs via an associative two-metal-aided catalytic mechanism" , J. Am. Chem. Soc., 130:10955-62 (2008).
Elbashir, et al., "Duplexes of 21-nucleotide RNAs mediate RNA interference in cultured mammalian cells" , Nature, 411:494-8 (2001).
Elkayam, et al., "The structure of human argonaute-2 in complex with miR-20a", Cell, 150:100-10 (2012).
Elsasser and Fels, "Atomistic details of the associative phosphodiester cleavage in human ribonuclease H" , Phys. Chem. Chem. Phys. 12:11081-8 (2010).
Ferre-D'Amare, et al., "Crystal structure of a hepatitis delta virus ribozyme" , Nature, 395:567-74 (1998).
Hassan, et al.,"High fidelity of base pairing by 2-selenothymidine in DNA" , J. Am. Chem. Soc., 132:2120-21 (2010).
Hendrickson, "Determination of macromolecular structures from anomalous diffraction of synchrotron radiation", Science, 254:51-8 (1991).
Hendrickson, "Synchrotron crystallography" , Trends Biochem. Sci., 25:637-43 (2000).

(Continued)

*Primary Examiner* — Suzanne M Noakes
(74) *Attorney, Agent, or Firm* — Pabst Patent Group LLP

(57) ABSTRACT

Methods for crystallizing a molecule of interest, such as a polypeptide, in complex with nucleic acid, including contacting the molecule of interest with selenium-derivatized nucleic acid and crystallizing the molecule of interest/selenium-derivatized nucleic acid complex are provided. Methods for determining the X-ray crystal structure of molecule of interest/selenium-derivatized nucleic acid complexes are also provided. Typically, the method of X-ray crystal structural determination includes selenium single-wavelength anomalous phasing of the selenium-derivatized nucleic acid. In some embodiments the phases for the X-ray crystal structure of the molecule of interest are not provided from another crystal. Also disclosed are methods of affecting a biological process by administering a functional nucleic acid to a cell or a subject and/or by bringing into contact a nuclease and a functional nucleic acid, where the functional nucleic acid is selenium-derivatized nucleic acid.

14 Claims, 7 Drawing Sheets

Specification includes a Sequence Listing.

(56) References Cited

OTHER PUBLICATIONS

Jiang, et al., "Selenium derivatization of nucleic acids for crystallography", Nucleic Acids Res, 35:2, 477-85 (2007).
Lee, et al., "An extensive class of small RNAs in Caenorhabditis elegans", Science, 294:862-4 (2001).
Lin, et al., "Nucleic acid X-ray crystallography via direct selenium derivatization", Chem. Soc. Rev., 40:4591-602 (2011).
Nowotny and Yang, "Stepwise analyses of metal ions in RNase H catalysis from substrate destabilization to product release", Embo J., 25:1924-33 (2006).
Nowotny, et al., "Crystal structures of RNase H bound to an RNA/DNA hybrid: substrate specificity and metal-dependent catalysis", Cell, 121:1005-16 (2005).
Nowotny, et al., "Specific recognition of RNA/DNA hybrid and enhancement of human RNase H1 activity by HBD", Embo J., 27:1172-81 (2008).
Olieric, et al., "A fast selenium derivatization strategy for crystallization and phasing of RNA structures", RNA, 15:4, 707-15 (2009).
Rosta, et al., "Catalytic mechanism of RNA backbone cleavage by ribonuclease H from quantum mechanics/molecular mechanics simulations", J. Am. Chem. Soc., 133:8934-41 (2011).
Ruigrok, et al., "Characterization of aptamer-protein complexes by X-ray crystallography and alternative approaches", Int J Mol Sci., 13:8, 10537-52 (2012).
Salon, et al., "Oxygen replacement with selenium at the thymidine 4-position for the Se base pairing and crystal structure studies", J. Am. Chem. Soc., 129:4862-3 (2007).
Salon, et al., "Derivatization of DNAs with selenium at 6-position of guanine for function and crystal structure studies", Nucleic Acids Res., 36:7009-18 (2008).
Schirle and Macrae, "The crystal structure of human Argonaute2", Science, 336:1037-40 (2012).
Sheng, et al., "Hydrogen bond formation between the naturally modified nucleobase and phosphate backbone", Nucleic Acids Res., 40:8111-8 (2012).
Storz, "An expanding universe of noncoding RNAs", Science, 296:1260-3 (2002).
Sun, et al., "Novel RNA base pair with higher specificity using single selenium atom", Nucleic Acids Res., 40:5171-9 (2012).
Ui-Tei, et al., "Sensitive assay of RNA interference in *Drosophila* and Chinese hamster cultured cells using firefly luciferase gene as target", FEBS Lett, 479:79-82 (2000).
Wilds, et al., "Selenium-assisted nucleic acid crystallography: use of phosphoroselenoates for MAD phasing of a DNA structure", J Am Chem Soc., 124:50, 14910-6 (2002).
Yang, et al., "Structure of ribonuclease H phased at 2 A resolution by MAD analysis of the selenomethionyl protein", Science, 249:1398-1405 (1990).
Zhang, et al., "Synthesis of 2'-deoxy-5-(methylselenyl)cytidine and Se-DNAs for structural and functional studies", Chem. Asian J., 7:476-9 (2012).

* cited by examiner

RNA-N: 3'-ACpAGCU-5'
DNA-N: 5'-ATG-TCGp-3'

Cleavage Site

```
           6 5 ↓ 4 3 2 1
RNA-N:   3'-A-C-p-AGCU-5'
DNA-Se:  5'-AT-SeG--TCGp-3'
           1 2   3  4 5 6
```

DNA-S: 5'-AT-SG---TCGp-3'

RNA-S1: 3'-AC-Sp-AGCU-5'
RNA-S2: 3'-AC-Rp-AGCU-5'

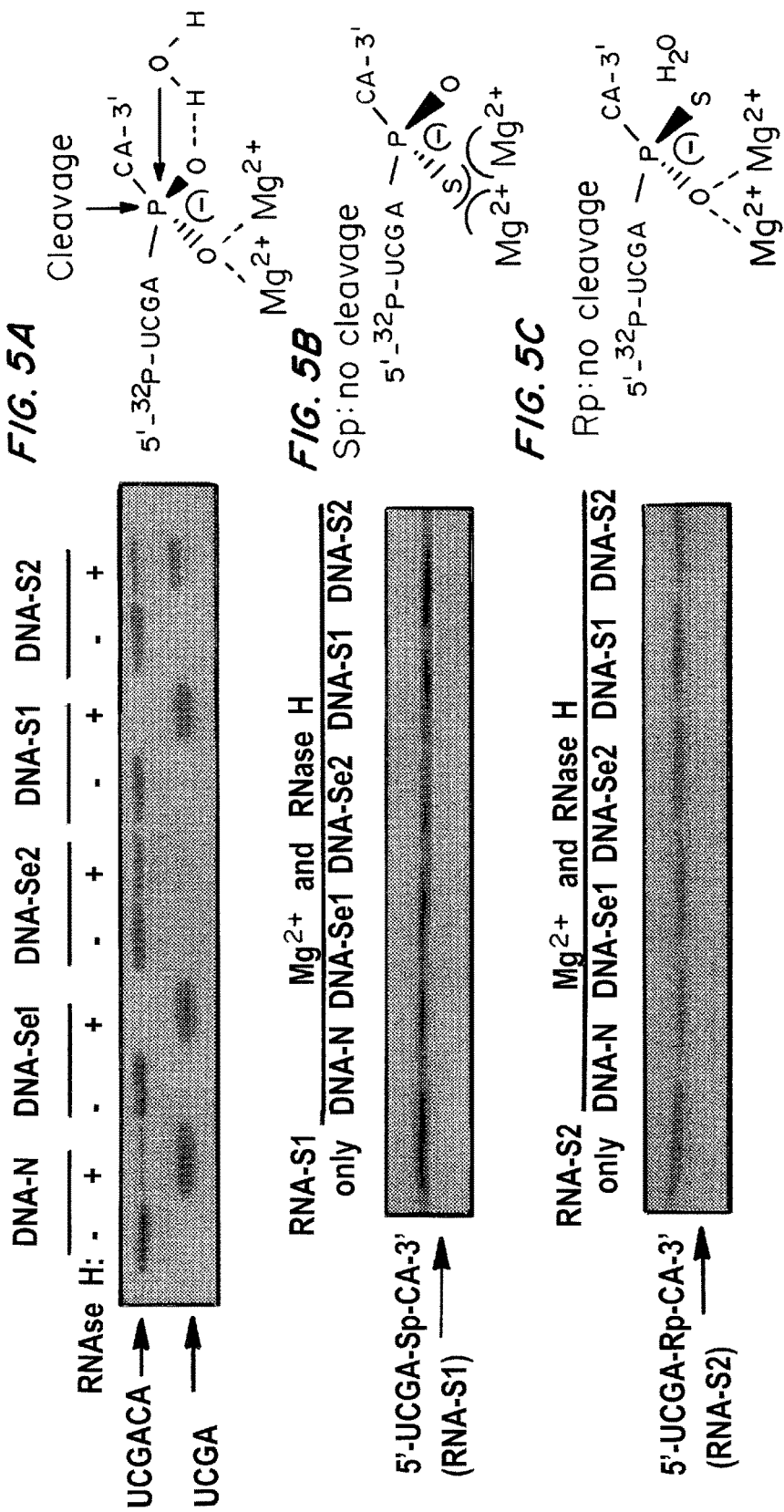

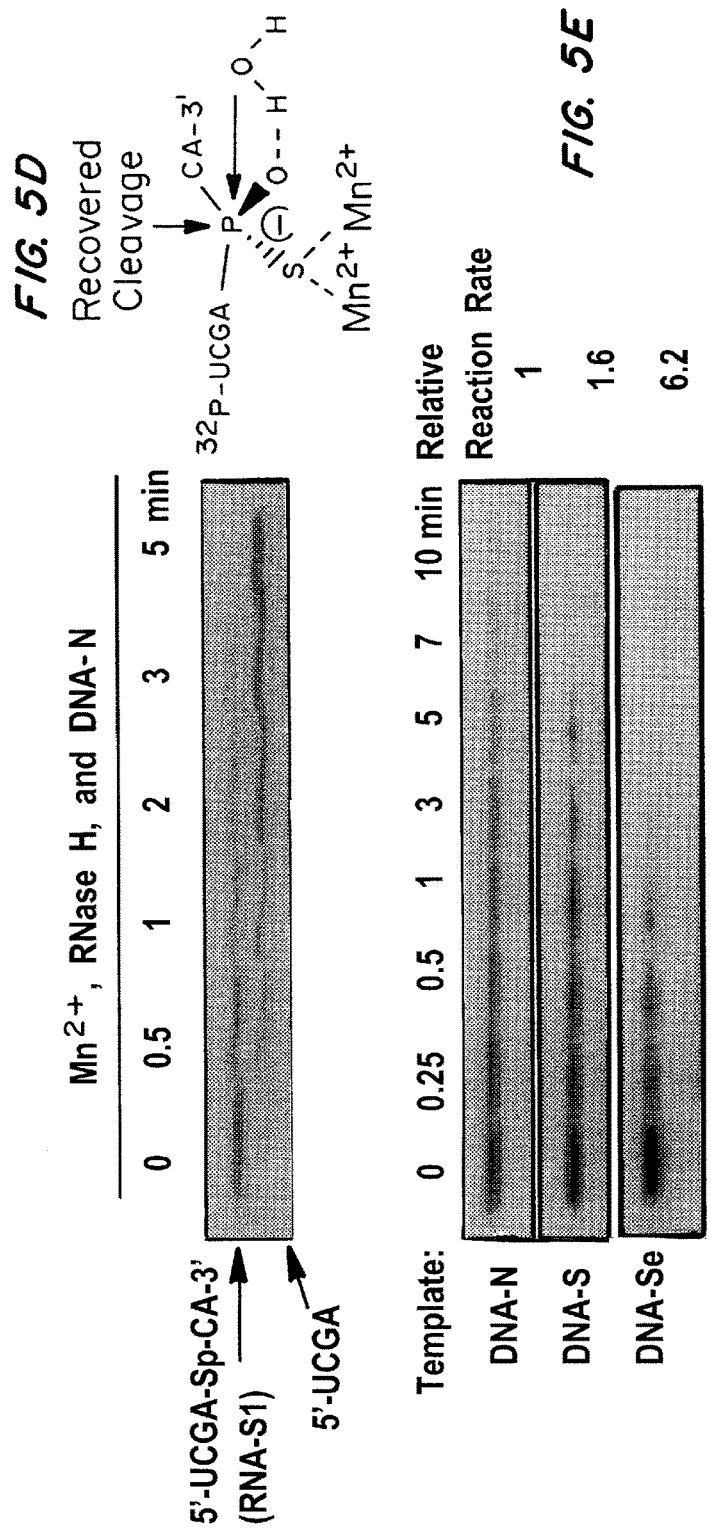

METHODS FOR STRUCTURAL DETERMINATION OF SELENIUM DERIVATIZED NUCLEIC ACID COMPLEXES

This application is a 371 application of International Application No. PCT/US2014/066823, filed Nov. 21, 2014, which claims benefit of and priority to U.S. Provisional Application No. 61/907,284, filed Nov. 21, 2013 and U.S. Provisional Application No. 61/909,732, filed Nov. 27, 2013.

STATEMENT REGARDING FEDERALLY SPONSORED RESEARCH OR DEVELOPMENT

This invention was made with Government Support under Grant R01GM095881 awarded by the National Institutes of Health and Grants MCB-0824837 and CHE-0750235 awarded by the National Science Foundation. The Government has certain rights in the invention.

REFERENCE TO SEQUENCE LISTING

The Sequence Listing submitted Mar. 15, 2019, as a text file named "SENAR_2014-12_ST25.txt" created on Jan. 23, 2019, and having a size of 859 bytes is hereby incorporated by reference pursuant to 37 C.F.R. § 1.52(e)(5).

FIELD OF THE INVENTION

The present invention is generally in the field of X-ray crystallography and drug discovery; and more specifically in the crystallography of molecule-nucleic acid structures, including protein and/or small molecule (ligand) complexes with nucleic acids, determined by selenium-derivatized nucleic acids. The structural information obtained can be used for the discovery of nucleic-acid based drugs.

BACKGROUND OF THE INVENTION

X-ray crystallography is an established, well-studied technique for providing a three-dimensional representation of the appearance of a molecule in a crystal. This technique remains one of the most powerful tools for atomic resolution determination of molecular structures. The crystalline atoms in a structure cause a beam of X-rays to diffract into many specific directions. By measuring the angles and intensities of these diffracted beams, a crystallographer can produce a three-dimensional picture of the density of electrons within the crystal. From this electron density, the mean positions of the atoms in the crystal can be determined, as well as their chemical bonds, their disorder and various other information.

Since many materials can form crystals—such as salts, metals, minerals, semiconductors, as well as various inorganic, organic and biological molecules—scientists have employed X-ray crystallography to determine the crystal structures of many molecules. The method reveals the structure and function of many biological molecules, including vitamins, drugs, small molecules, ligands, proteins, polypeptides, and nucleic acids. X-ray crystal structures can also account for unusual electronic or elastic properties of a material, shed light on chemical interactions and processes, or serve as the basis for designing pharmaceuticals against diseases.

In order to perform an X-ray crystallographic analysis, a beam of X-rays strikes a single crystal, producing scattered beams. When they land on a piece of film or other detector, these beams make a diffraction pattern of spots; the strengths and angles of these beams are recorded as the crystal is gradually rotated. Each spot is called a reflection, since it corresponds to the reflection of the X-rays from one set of evenly spaced planes within the crystal. The atoms in a crystal are not static, but oscillate about their mean positions, usually by less than a few tenths of an angstrom. X-ray crystallography allows measuring the size of these oscillations.

X-rays that are diffracted from a crystal of a molecule give rise to a pattern of diffraction "spots", with each spot corresponding to a point in the reciprocal crystal lattice, representing a wave with an amplitude and a relative phase. Structure factors corresponding to the reciprocal crystal lattice also correspond to the electron density distribution within the crystallographic "unit cell." Electron density corresponding to the structure factors can be determined by an inverse Fourier transformation. The calculation of a useful electron density map requires combining the observed amplitudes with correct phases.

Determination of the phase for structure factors remains the most challenging obstacle for the crystallographic analyses of molecules, such as proteins, and complexes. New methods to enable the determination of phases for X-ray diffraction data to be used in structural analyses are sought.

Nucleic acids play a variety of important roles in biological systems, including the transfer and regulation of genetic information (Ban et al., Science, 289:905-920 (2000)). Moreover, nucleic acids, especially RNAs, can fold into well-defined three-dimensional structures and catalyze biochemical reactions in processes such as protein synthesis and in the life cycle of some viruses. RNAs and DNAs with catalytic and binding functions have also been identified via in vitro selection. Furthermore, the recent discovery of noncoding small RNAs in diverse organisms has enormously expanded the repertoire of functions of nucleic acids (Storz, Science, 296:1260-1263 (2002); Lee et al., Science, 294:862-864 (2001)). This vast array of biologically active RNAs and DNAs has promoted a new front of research in the field of structural analysis to elucidate their three-dimensional structure and functional relationships.

As ubiquitous biological molecules in all living systems, nucleic acids are important drug targets, and they can also be used in diagnostics and therapeutics.

The X-ray crystallographic analyses of nucleic acids and the molecules to which they bind are often difficult and can be time and labor-intensive, owing to problems with the production and diffraction quality of crystals containing molecule/nucleic acid complexes.

Therefore, it is an object of the invention to provide compositions and methods for the production of crystals and determination of X-ray crystal structures of molecules of interest, such as proteins, complexed with nucleic acids.

It is another object of the invention to provide compositions and methods for selecting and designing molecules that can bind to molecules of interest, such as proteins, that are or can complex with nucleic acids.

It is another object of the invention to provide complexes of molecules of interest, such as proteins, and selenium-derivatized nucleic acids.

SUMMARY OF THE INVENTION

Methods for crystallizing a molecule of interest, such as a polypeptide, in complex with nucleic acid, including contacting the molecule of interest with selenium-derivatized nucleic acid and crystallizing the molecule of interest/ selenium-derivatized nucleic acid complex are provided. Methods for determining the X-ray crystal structure of molecule of interest/selenium-derivatized nucleic acid complexes are also provided. Typically, the method of X-ray crystal structural determination includes selenium single-wavelength anomalous phasing of the selenium-derivatized nucleic acid. In some embodiments the phases for the X-ray crystal structure of the molecule of interest are not provided from another crystal.

In some embodiments, the complex can include one or more additional components. For example, the complex can comprise the molecule of interest, selenium-derivatized nucleic acid, and ligand or binding molecule. For example, a compound that binds to either or both the molecule of interest and the selenium-derivatized nucleic acid can be used. Small molecule ligands and candidate drugs are examples of extra components that can be used.

In some embodiments the resolution of diffraction of the X-ray crystallographic data obtained with crystals containing selenium-derivatized nucleic acid complex is greater than that of crystallographic data obtained with crystals that do not contain a selenium-derivatized nucleic acid. In other embodiments, the molecule of interest does not crystallize in the absence of selenium-derivatized nucleic acid. Typically, the selenium-derivatized nucleic acid is selenium-derivatized RNA. In some embodiments the selenium-derivatized nucleic acid binds to a target molecule, such as a polypeptide, with at least the same affinity as nucleic acid that is not selenium-derivatized. In one embodiment selenium-derivatized nucleic acid binds the same region of the target molecule as nucleic acid that is not selenium-derivatized. In some embodiments the molecule of interest is a nucleic acid-binding protein.

Methods of determining the structure of a molecule of interest, such as a protein, in complex with a nucleic acid derivatized with selenium include obtaining a diffraction dataset from one or more crystals containing a complex containing the molecule of interest/selenium-derivatized nucleic acid and determining the three dimensional X-ray crystal structure of the molecule of interest/selenium-derivatized nucleic acid complex by selenium single-wavelength anomalous phasing of the selenium-derivatized nucleic acid. Methods of identifying the interfacing elements between the molecule of interest and selenium-derivatized nucleic acid in the three dimensional X-ray crystal structure of the molecule of interest/selenium-derivatized nucleic acid complex are also provided. The methods can also include selecting a molecule, such as a candidate drug, which interferes with the interaction between molecule of interest and nucleic acid, by providing, on a digital computer, the three-dimensional X-ray crystal structure of the molecule of interest/selenium-derivatized nucleic acid complex and selecting a compound predicted to bind the nucleic acid interface identified in the molecule of interest/selenium-derivatized nucleic acid complex structure.

Methods for designing a molecule, such as a candidate drug, which binds to the molecule of interest, such as a nucleic acid-binding protein, are also provided. Typically the methods include providing on a digital computer the three-dimensional crystal structure of a molecule of interest/ selenium-derivatized nucleic acid complex and using software comprised by the digital computer to design a molecule, such as a candidate drug, which is predicted to bind to the molecule of interest. In some embodiments the methods include synthesizing the molecule and evaluating the molecule for an ability to alter an activity of the molecule of interest.

Methods of selecting crystals containing selenium-derivatized nucleic acid, including growing crystals in a solution containing selenium-derivatized nucleic acid and selecting crystals that are visibly distinct from control crystals, indicating the presence of selenium-derivatized nucleic acid, are also provided.

Complexes of a molecule of interest and a selenium-derivatized nucleic acid are also provided. Complexes of a polypeptide and a selenium-derivatized nucleic acid are also provided.

Also disclosed are methods of affecting a biological process, the method comprising administering a functional nucleic acid to a cell or a subject, where the functional nucleic acid is selenium-derivatized nucleic acid. Also disclosed are methods of affecting a biological process by bringing into contact a nuclease and a functional nucleic acid, where the functional nucleic acid is selenium-derivatized nucleic acid.

In some forms of the method, the functional nucleic acid can be an aptamer, an antisense nucleic acid, an siRNA, an shRNA, or a crRNA. In some forms of the method, the functional nucleic acid can bind to or affect a molecule of interest. In some forms, the functional nucleic acid can be a substrate or cofactor for a nuclease. In some forms, the cofactor can be a substrate-guiding sequence (or guide), which directs a nuclease to cleave a substrate (an RNA or DNA). In some forms, catalytic activity of the nuclease is increased in the presence of the selenium-derivatized nucleic acid compared to catalytic activity of the nuclease in the presence of a corresponding nucleic acid that is not selenium-derivatized. For example, the comparison catalytic activity can be the catalytic activity of the nuclease in the presence of the corresponding native nucleic acid. The nuclease can be any type or form of nuclease.

BRIEF DESCRIPTION OF THE DRAWINGS

FIG. 5 shows "pseudo-specific" cleavage of RNA substrates by RNase H. RNase H cleavage of short native and modified RNA substrates in the presence of the short native and modified DNA guides (see sequences in FIG. 1). In the reactions, the concentration of RNA substrate was equal to that of the native, single-Se, double-Se, single-S, or double-S modified DNAs. Truncated RNase H (59-196) was also used for these experiments, and similar results were obtained. (Panel A) Cleavage of the native RNA by RNase H in the presence of the native and modified DNAs. (Panel B) Cleavage inhibition by the Sp-sulfur modification of the RNA substrate (RNA-S1, Sp diastereomer). (Panel C) Cleavage inhibition by the Rp-sulfur modification of the RNA substrate (RNA-S2, Rp diastereomer). (Panel D) Recovery of Sp-RNA cleavage by replacing $Mg^{2+}$ with $Mn^{2+}$ cations. (Panel E) RNA hydrolysis by RNase H in the presence of DNA guides, including the native DNA-N, DNA-S, and DNA-Se. The relative values of the reaction rates using these templates are: DNA-N(1), DNA-S(1.6), and DNA-Se (6.2).

DETAILED DESCRIPTION OF THE INVENTION

Figures 1A, 1B:
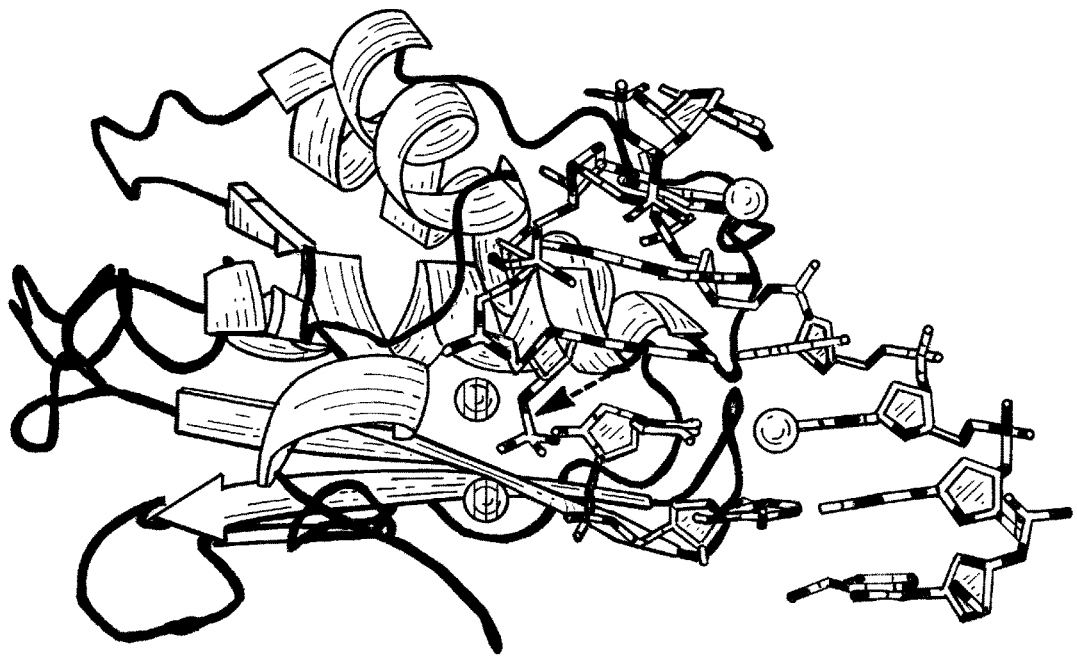
FIGS. 1A, 1B, and 1C show the crystal structure of RNase H complexed with the selenium-modified DNA and RNA duplex. (A) The overall structure of selenium-DNA/RNA/ RNase H ternary complex determined at 1.80 Å resolution (D132N mutant; PDB ID: 3TWH). Protein is shown as a ribbon diagram; RNA strands are shown in ball and stick format on the left overlapping with the protein structure; and DNA strands are in ball and stick format on the right protruding from the structure. The spheres represent $Mg^{2+}$ ions and Se atoms, as indicated. The cleavage site is indicated by the arrow. (B) Sequences of the native and modified DNAs and RNAs. $^{Se}G$ and $^{S}G$ represent 6-Se-G and 6-S-G, respectively. (C) The Se-DNA derivatized with the 6-Se-deoxyguanosine.

X-ray crystal structures of proteins and protein-nucleic acid complexes are commonly determined by selenium-derivatized (i.e. selenomethionyl) proteins via multi- or single-wavelength anomalous diffraction (MAD or SAD) phasing. MAD phasing is a technique used in X-Ray crystallography that facilitates the determination of the three-dimensional structure of biological macromolecules (such as DNA or drug receptors) via solution of the phase problem. Methods of substituting carbonyl oxygens in nucleic acid bases with selenium atoms have been discovered. It has also been discovered that selenium-derivatized nucleic acids retain binding characteristics of non-derivatized nucleic acids. It has also been discovered that selenium-derivatized nucleic acids complexed with molecules of interest, such as polypeptides, can aid in crystallization and with X-ray crystallographic determination of the structure of such complexes. Disclosed are methods of crystallizing a molecule of interest, such as a polypeptide, in complex with nucleic acid, comprising the steps of (a) contacting the molecule of interest with selenium-derivatized nucleic acid; and (b) crystallizing the molecule of interest/selenium-derivatized nucleic acid complex. The method can further comprise the step of determining the X-ray crystal structure of the molecule of interest/selenium-derivatized nucleic acid complex. The X-ray crystal structural determination can comprise selenium single-wavelength anomalous phasing of the selenium-derivatized nucleic acid.

Also disclosed are methods of determining the interaction between a molecule of interest, such as a polypeptide, and nucleic acid, comprising the steps of (a) contacting the molecule of interest with a selenium-derivatized nucleic acid; (b) crystallizing the molecule of interest/selenium-derivatized nucleic acid complex; (c) determining the three dimensional X-ray crystal structure of the molecule of interest/selenium-derivatized nucleic acid complex, wherein the method of X-ray crystal structural determination comprises selenium single-wavelength anomalous phasing of the selenium-derivatized nucleic acid; and (d) identifying the interfacing elements between the molecule of interest and selenium-derivatized nucleic acid in the three dimensional X-ray crystal structure of the molecule of interest/selenium-derivatized nucleic acid complex.

The method can further comprise selecting a molecule, such as a candidate drug, which interferes with the interaction between the molecule of interest and the nucleic acid. The molecule can be selected by (a) providing on a digital computer the three-dimensional X-ray crystal structure of the molecule of interest/selenium-derivatized nucleic acid complex; and (b) selecting a compound predicted to bind the nucleic acid interface identified in the molecule of interest/selenium-derivatized nucleic acid complex structure.

The method can further comprise designing a molecule, such as a candidate drug, which binds to the molecule of interest. The molecule can be designed by (a) providing on a digital computer the three-dimensional crystal structure of the molecule of interest/selenium-derivatized nucleic acid complex; and (b) using software comprised by the digital computer to design a molecule which is predicted to bind to the molecule of interest.

The method can further comprise (a) synthesizing the molecule; and (b) evaluating the molecule for an ability to alter an activity of the molecule of interest.

In some forms of the method, the resolution of diffraction of the X-ray crystallographic data obtained with the selenium-derivatized nucleic acid complex can be greater than that of crystallographic data obtained in the absence of selenium-derivatized nucleic acid. In some forms of the method, the molecule of interest does not crystallize in the absence of selenium-derivatized nucleic acid. In some forms of the method, phases for the X-ray crystal structure of the molecule of interest are not provided from another crystal. In some forms of the method, the molecule of interest is not a nucleic acid-binding protein.

Also disclosed are methods of selecting crystals containing selenium-derivatized nucleic acid, comprising the steps of (a) growing crystals in a solution containing selenium-derivatized nucleic acid; and (b) selecting crystals that are colored yellow, indicating the presence of selenium-derivatized nucleic acid. In some forms of the method, the color of crystals containing selenium-derivatized nucleic acid is compared to the color of control crystals that do not contain selenium-derivatized nucleic acid. In some forms of the method, the selenium-derivatized nucleic acid can be in complex with a molecule of interest. In some forms of the method, the selenium-derivatized nucleic acid can be in complex with a polypeptide.

In some forms of the method, the selenium-derivatized nucleic acid can be selenium-derivatized RNA. In some forms of the method, the selenium-derivatized nucleic acid can bind to the molecule of interest with at least the same affinity as nucleic acid that is not selenium-derivatized. In some forms of the method, the selenium-derivatized nucleic acid can bind the same region of the molecule of interest as nucleic acid that is not selenium-derivatized.

Also disclosed are complexes of a molecule of interest and a selenium-derivatized nucleic acid. Also disclosed are complexes of a polypeptide and a selenium-derivatized nucleic acid.

I. Definitions

Unless defined otherwise, all technical and scientific terms used herein have the same meanings as commonly understood by one of skill in the art to which the disclosed invention belongs. Publications cited herein and the materials for which they are cited are specifically incorporated by reference.

The term DNA-binding protein refers to proteins that are composed of DNA-binding domains and thus have a specific or general affinity for either single or double stranded DNA. Exemplary DNA-binding proteins are transcription factors which modulate the process of transcription, various polymerases, nucleases which cleave DNA molecules within a crystal, and histones which are involved in chromosome packaging and transcription in the cell nucleus.

The term interfacing elements refers to elements that may be necessary for the interaction between the selenium-derivatized nucleic acid and the protein it binds.

The term multi-wavelength anomalous diffraction (MAD) phasing refers to a technique that facilitates the determination of the three-dimensional structure of biological macromolecules (e.g., DNA, drug receptors). This method doesn't need two crystal structures (one native and one with a heavy atom) for a unique phase solution. Instead, anomalous diffraction is recorded at different wavelengths of coherent X-ray light at a synchrotron facility.

The term nucleic acid-binding protein refers to proteins that contain nucleic acid-, DNA-, or RNA-binding domains and thus have specific or general affinity for nucleic acids, DNA, or RNA. Exemplary nucleic acid-binding proteins are DNA-binding proteins and RNA-binding proteins.

The term phase refers to the position of a wave's maximum relative to an origin.

The term molecule of interest refers to any compound or molecule, including biological molecules, such as vitamins, drugs, small molecules, ligands, proteins, polypeptides, and nucleic acids.

The term molecule of interest/selenium-derivatized RNA complex refers to the complex formed between the selenium-derivatized RNA and a molecule of interest.

The term polypeptide/selenium-derivatized RNA complex refers to the complex formed between the selenium-derivatized RNA and a polypeptide of interest.

The term resolution of diffraction refers to the sharpness of features in the electron density of the molecule, as well as the certainty about the position of atoms. The greater the resolution, the better the quality of the image.

The term RNA-binding protein refers to proteins that contain RNA-binding domains and thus have specific or general affinity for RNA. Exemplary RNA-binding proteins are proteins involved in the control of alternative splicing, RNA editing, polyadenylation, nuclear export, mRNA localization and translation.

The term selenium-derivatization refers to the use of selenium to replace sulfur in methionine or oxygen in nucleotides in order to mimic methionine or natural nucleotides, respectively. Selenium can thus be used as an atomic probe for structure and function studies of nucleic acids.

The term selenium-derivatized nucleic acid refers to nucleic acids that contain selenium in place of oxygen.

The term selenium-derivatized DNA refers to DNAs that contain selenium in place of oxygen.

The term selenium-derivatized RNA refers to RNAs that contain selenium in place of oxygen.

The term shRNA refers to short hairpin RNA, an RNA structure that forms a tight hairpin turn, which can also be used to silence gene expression via RNA interference. The shRNA hairpin structure is cleaved by the cellular machinery into small interfering RNA (siRNA), which is then bound to the RNA-induced silencing complex (RISC). This complex binds to and cleaves mRNA, which matches the siRNA that is bound to it.

The term single-wavelength anomalous diffraction (SAD) phasing refers to a technique that facilitates the determination of the structure of molecules of interest, such as proteins or other biological macromolecules. In contrast to multi-wavelength anomalous diffraction (MAD), SAD uses a single dataset at a single appropriate wavelength. One advantage of the technique is the minimization of time spent in the beam by the crystal, thus reducing potential radiation damage to the molecule while collecting data.

The term siRNA refers to a small interfering RNA, commonly 18 to 30 nucleotides, preferably 20 to 25, more preferably 21 to 23, or approximately 22 nucleotide double-stranded RNA. Preferably at least one strand has a 5'- and/or 3' overhang of 1 to 5, preferably 1 to 3, or 2 nucleotides. siRNA is involved in the RNA interference pathway where the siRNA interferes with the expression of a specific gene.

The term three dimensional X-Ray crystal structure refers to the structure resulting from X-ray crystallography (synonymous with "crystal" above).

The term X-ray crystallography refers to the method used for determining the atomic and molecular structure of a crystal, in which the crystalline atoms cause a beam of X-rays to diffract into many specific directions. By measuring the angles and intensities of these diffracted beams, a crystallographer can produce a three-dimensional picture of the density of electrons within the crystal.

The term X-ray diffraction refers to the technique involving a stream of X-rays from an X-ray source that diffract and scatter as they encounter the atoms of molecules within a crystal.

II. Compositions

A. Selenium-Derivatized Nucleic Acids

The disclosed compositions and methods make use of selenium-derivatized nucleic acids. Selective replacement of oxygen atoms in nucleotide residues of nucleic acids produces selenium-derivatized nucleic acids. Uses and advantages of such selenium-derivatized nucleic acids are described herein.

Selenium atom-specific replacement on the nucleobases (Hassan et al., J. Am. Chem. Soc., 132:2120-2121 (2010); Lin et al., Chem. Soc. Rev., 40:4591-4602 (2011); Salon et al., Nucleic Acids Res., 36:7009-7018 (2008); Salon et al., J. Am. Chem. Soc., 129:4862-4863 (2007); Sheng et al., Nucleic Acids Res., 40:8111-8118 (2012); Sun et al., Nucleic Acids Res., 40:5171-5179 (2012); Zhang et al., Chem. Asian J., 7:476-479 (2012)), can be used to produce selenium-derivatized nucleic acids.

B. Functional Nucleic Acids

Selenium derivatizations and selenium-derivatized nucleic acids can be embodied in functional nucleic acids. Substitution with selenium for one or more oxygen atoms in a nucleic acid or within one or more nucleotide residues in a nucleic acid can provide nucleic acids with useful properties, such as improved hybridization accuracy, thermostability, chemical, biochemical and biological stability, activity efficiency, facilitated crystallization, facilitated phase determination, and enhanced high-resolution crystal structure determination.

Functional nucleic acids are nucleic acid molecules that have a specific function, such as binding a target molecule, serving as an enzyme substrate or cofactor, or catalyzing a specific reaction. For example, functional nucleic acids can bind a target nucleic acid (RNA or DNA) or can serve as enzyme substrate-guiding sequence (or guide). Functional nucleic acid molecules can be divided into the following categories, which are not meant to be limiting. For example, functional nucleic acids include antisense molecules, aptamers, ribozymes, triplex forming molecules, RNA interference (RNAi), CRISPR (Clustered Regularly Interspaced Short Palindromic Repeats) RNA (crRNA), and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Often functional nucleic acids are designed to interact with other nucleic acids based on sequence complementarity between the target molecule and the functional nucleic acid molecule. In other situations, the specific recognition between the functional nucleic acid molecule and the target molecule is not based on sequence complementarity between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNase H mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than 10-6, 10-8, 10-10, or 10-12. Representative examples of how to make and use triplex forming molecules to bind a variety of different target molecules can be found in U.S. Pat. Nos. 5,176,996, 5,645,985, 5,650,316, 5,683,874, 5,693,773, 5,834,185, 5,869,246, 5,874,566, and 5,962,426.

Gene expression can also be effectively silenced in a highly specific manner through RNA interference (RNAi). This silencing was originally observed with the addition of double stranded RNA (dsRNA) (Fire, A., et al., Nature, 391:806-11 (1998); Napoli, C., et al., Plant Cell, 2:279-89 (1990); Hannon, G. J., Nature, 418:244-51 (2002)). Once dsRNA enters a cell, it is cleaved by an RNase III-like enzyme, Dicer, into double stranded small interfering RNAs (siRNA) 21-23 nucleotides in length that contain 2 nucleotide overhangs on the 3' ends (Elbashir, S. M., et al., Genes Dev., 15:188-200 (2001); Bernstein, E., et al., Nature, 409: 363-6 (2001); Hammond, S. M., et al., Nature, 404:293-6 (2000)). In an ATP-dependent step, the siRNAs become integrated into a multi-subunit protein complex, commonly known as the RNAi induced silencing complex (RISC), which guides the siRNAs to the target RNA sequence (Nykanen, A., et al., Cell, 107:309-21 (2001)). At some point the siRNA duplex unwinds, and it appears that the antisense strand remains bound to RISC and directs degradation of the complementary mRNA sequence by a combination of endo and exonucleases (Martinez, J., et al., Cell, 110:563-74 (2002)). However, the effect of RNAi or siRNA or their use is not limited to any type of mechanism.

Small Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al., Nature, 411:494 498(2001); Ui-Tei, K., et al., FEBS Lett, 479:79-82 (2000)). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

Similar to RNAi, CRISPR (Clustered Regularly Interspaced Short Palindromic Repeats) interference is a powerful approach, via selective DNA cleavage, for reducing gene expression of endogenously expressed proteins. CRISPRs are genetic elements containing direct repeats separated by unique spacers, many of which are identical to sequences found in phage and other foreign genetic elements. Recent work has demonstrated the role of CRISPRs in adaptive immunity and shown that small RNAs derived from CRISPRs (crRNAs) are implemented as homing oligonucleotides for the targeted interference of foreign DNA (Jinek et al., Science, 337:816-821 (2012)). crRNAs are used to selectively cleave DNA at the genetic level.

Where the functional nucleic acid serves as an enzyme cofactor, the cofactor can be, for example, a substrate-guiding sequence (or guide), which directs a nuclease to cleave a substrate (an RNA or DNA).

III. Methods of Use

A. Methods of X-Ray Crystallography

It has been discovered that nucleic acids derivatized with selenium (Se) can be used to determine the X-ray crystal structures of nucleic acids and their complexes with molecules of interest, such as proteins and ligands, via Se-nucleic acid multiple anomalous diffraction (MAD) phasing. Methods for enhanced crystallization and structural determination of X-ray crystal structures using selenium-derivatized nucleic acids and their complexes with molecules of interest are described.

Nucleic acids derivatized with selenium can be used to provide phase information for the determination of the crystal structures of molecules of interest, such as proteins, to which they are bound. Methods for the use of nucleic acids derivatized with selenium to provide phasing information for RNA/DNA-molecule complexes are provided.

Furthermore, X-ray crystal structures determined by phases obtained from selenium-derivatized nucleic acids can be used for structure-based drug design and the selection of drug candidates.

1. Crystallization

The technique of X-ray crystallography has three basic steps. The first and often most difficult is to obtain an adequate crystal of the material under study. The crystal should be sufficiently large (typically larger than 0.1 mm in all dimensions), pure in composition and regular in structure, with no significant internal imperfections.

In the second step, the crystal is placed in an intense beam of X-rays, usually of a single wavelength, producing a regular pattern of reflections. As the crystal is gradually rotated, previous reflections disappear and new ones appear; the intensity of every spot is recorded at every orientation of the crystal. Multiple data sets may have to be collected, with each set covering slightly more than half a full rotation of the crystal and typically containing tens of thousands of reflections.

In the third step, these data are combined computationally with complementary chemical information to produce and refine a model of the arrangement of atoms within the crystal. The final, refined model of the atomic arrangement—now called a crystal structure—is usually stored in a public database.

The methods and compositions disclosed herein can be used to enable, enhance or optimize the process of crystallization. Protein crystallization is a widely used technique for obtaining the atomic three dimensional structure of a protein. However, optimal crystallization conditions are impossible to predict, and must be individually determined for each protein for the production of crystals amenable to high-resolution X-ray diffraction. As such, crystallization often represents a barrier to the structural determination of macromolecules, such as proteins and protein complexes.

Thus, in some embodiments the disclosed nucleic acids derivatized with selenium are used to facilitate the crystallization of molecules of interest, such as proteins or ligands, to which they are attached. Nucleic acids can interact with proteins, polypeptides and other ligands to form complexes with altered structural features and properties. Nucleic acids may give rise to conformational changes in peptides, proteins or other ligands with which they interact. Accordingly, if nucleic acids derivatized with selenium induce or otherwise impart structural properties favorable for crystallization of the peptides, proteins or other ligands with which they interact, it is desirable to form complexes with nucleic acids derivatized with selenium for the purposes of crystallization. Structural properties that assist in the process of crystallization can include oligomeric state, enhanced or reduced flexibility of a region of a molecule, peptide, protein or other ligand, enhanced or reduced rigidity of a region of a molecule, peptide, protein or other ligand, altered solubility, altered hydrophobicity or ability to bind to other molecules, peptides, proteins or ligands.

The crystallization of nucleic acids derivatized with selenium in complex with molecules, proteins, polypeptides or other ligands can be compared to a control. A typical control includes a complex of the same molecule, protein, polypeptide or other ligand with an equivalent nucleic acid that is not derivatized with selenium.

In some embodiments, complexes with nucleic acids derivatized with selenium form crystals where the controls do not. In some embodiments complexes with nucleic acids derivatized with selenium provide enhanced nucleation of crystals as compared to controls. In other embodiments crystals containing nucleic acids derivatized with selenium provide a greater resolution of diffraction of X-rays than controls.

Another challenge in the crystallization of proteins is the identification of crystals that contain the desired target protein or protein complex. Crystals containing protein salt, contaminants, degradation products or single substrates of complexes can delay or prevent the crystallographic determination of target proteins. The same can apply to other target molecules. Accordingly, the ability to visually identify crystals that contain nucleic acids derivatized with selenium can assist in the selection and screening of complexes containing derivatized RNA or DNA. Nucleic acid derivatized with selenium can be visibly distinct from nucleic acid that is not derivatized with selenium, for example, by having a different color. In some embodiments crystals of complexes with nucleic acids derivatized with selenium are visibly distinct from crystals of controls. In some embodiments differences in the color of crystals containing nucleic acids derivatized with selenium enable the rapid selection of crystals that contain nucleic acids derivatized with selenium.

Crystals containing nucleic acids derivatized with selenium can be produced by methods including, but not limited to co-crystallization of the nucleic acids and molecule of interest (such as proteins), crystallization of the purified nucleic acid/molecule complexes, or by soaking crystals of the molecule of interest into a solution containing the nucleic acids derivatized with selenium.

2. Structural Determination

The methods and compositions disclosed herein can be used to enable, enhance or optimize the process of structural determination. Methods for the determination of X-ray crystal structures of proteins derivatized with seleno-methionine are well known in the art. After the SAD or MAD dataset is collected from a single crystal, the selenium atoms can be located by direct methods and phases can be determined similarly to the well-established protein strategy (Elkayam et al., Cell, 150:100-110 (2012); Ferre-D'Amare et al., Nature, 395:567-574 (1998); Hendrickson, Science, 254:51-58 (1991); Hendrickson, Trends Biochem. Sci., 25:637-643 (2000); Schirle and MacRae, Science, 336:1037-1040 (2012); Yang et al., Science, 249:1398-1405 (1990)).

Similar to the selenium substitution of the sulfur atoms in protein, the oxygen atoms in nucleic acids can be replaced with selenium atoms, since selenium and oxygen are also in the same elemental family. This Se atom-specific derivatization is also called Se atom-specific mutagenesis (SAM). SAM can be used to provide new insights into both structure and function of proteins and protein complexes.

Methods for the determination of phases are known in the art and include Molecular Replacement using prior structural information of a similar molecule and isomorphous replacement to alter the structure factors in a known way, for example, by including heavy atoms with a large atomic number. Inclusion of heavy atoms within a molecule will increase the scattering of X-rays significantly. The differences in scattered intensities will largely reflect the scattering contribution of the heavy atoms, and these differences can be used to determine where the heavy atoms are located within the electron density map. It is important that the inclusion of heavy atoms does not otherwise alter the structure of the molecule, to enable isomorphous replacement.

Methods to determine a three-dimensional structure of a target molecule structure in complex with nucleic acids derivatized with selenium, in which the three-dimensional structure of the target molecule is not known are provided. In some embodiments the methods are useful for determining the X-ray crystal structures of molecules that bind nucleic acids based only on the identification of the selenium atoms within the derivatized nucleic acids.

Therefore, methods for the use of nucleic acids derivatized with selenium to provide phasing information for the crystallographic determination of molecule complexes bound to the nucleic acids derivatized with selenium are provided. The methods can involve recording the anomalous diffraction of X-rays at different wavelengths of coherent X-ray light from crystals containing nucleic acids derivatized with selenium and locating the selenium atoms to determine phase information for the molecule bound to the nucleic acids. In some embodiments, the molecule is an enzyme. Such enzymes can include, but are not limited to RNA and DNA-binding enzymes. An exemplary RNA-binding enzyme is RNase H. In certain embodiments the structure of the target molecule is not known. In some embodiments, the target molecule is a target protein. In some embodiments the amino acid sequence of the target protein does not contain the amino acid methionine. In other embodiments, the amino acid sequence of the target protein contains less than 5%, less than 3% or less than 1% methionine. In some embodiments the amino acid sequence of the target protein is less than 60%, less than 50%, less than 40%, less than 30%, less than 20%, or less than 10% identical to the amino acid sequence of the most similar protein for which a crystal structure exists.

In some embodiments, X-ray crystal structures of complexes containing nucleic acids derivatized with selenium are used, for example, in methods of structure-based drug design. In some embodiments, the X-ray crystal structures are used in the determination of the biological functions of the complexes. Structural information for molecules identified by these methods may be used for the design, identification or selection of drugs, for example for use in therapeutic compositions. In some embodiments the methods enable faster processing and increased throughput in discovery of three dimensional structures for the purposes of drug design.

The described methods for the production and determination of the three dimensional coordinates of crystals containing nucleic acids derivatized with selenium have the advantage of convenient determination of phases using the selenium within derivatized nucleic acids. In some embodiments the methods enable the determination of crystal structures of molecules of interest, such as proteins, that interact with DNA or RNA. In certain embodiments crystallographic data collection is carried out at a synchrotron facility. Data collection may be carried out at above freezing temperatures. Data collection can also be carried out temperatures 0° C., such as at the temperature of liquid nitrogen, at approximately −190° C., or liquid helium, at approximately −270° C.

B. Methods of Using Altered Nucleic Acids

In addition to their utility in structural studies, selenium atoms can be atom-specifically incorporated into nucleic acids for functional studies as well, via selective oxygen replacement.

Nucleic acids are polymeric macromolecules, essential for all known forms of life. Nucleic acids, which include deoxyribonucleic acid (DNA) and ribonucleic acid (RNA), are made from monomers known as nucleotides. Each nucleotide has three components: a 5-carbon sugar, a phosphate group, and a nitrogenous base. If the sugar is deoxyribose, the polymer is DNA. If the sugar is ribose, the polymer is RNA.

RNA can also include noncoding RNA (ncRNA), such as small interfering RNA (siRNA), micro RNA (miRNA), ribosomal RNA (rRNA), transfer RNA (tRNA), small nucleolar RNA (snoRNA), short hairpin RNA (shRNA), and small nuclear RNA (snRNA), among others.

It has been determined that nucleic acids derivatized with selenium can alter the activity of proteins with which the nucleic acids interact. Typically, the protein is an enzyme that catalyzes changes in the structure of the nucleic acid. In some embodiments, the presence of selenium within nucleic acid derivatized with selenium does not alter the biological functions associated with the tertiary structure of the nucleic acid.

Biological functions associated with the tertiary structure of the nucleic acid can include, but are not limited to, interaction with nucleic acids or proteins such as enzymes. In some embodiments, the presence of selenium imparts changes in the tertiary structure of the nucleic acid that increase the half-life or structural rigidity of the nucleic acid. Typically, the presence of selenium within the derivatized polynucleotides does not inhibit, prevent or reduce interaction of the derivatized nucleic acids with proteins such as RNA or DNA binding enzymes. In certain embodiments, nucleic acids derivatized with selenium increase the rate of catalysis of proteins such as RNA or DNA binding enzymes. In one embodiment, enzyme catalysis of nucleic acids derivatized with selenium is facilitated by a local subtle unwinding of a DNA/RNA duplex. The subtle structural changes can, for example, shift the RNA scissile phosphate closer to the enzyme active site.

Accordingly, methods for the use of nucleic acids derivatized with selenium in altering the activities of nucleic acid binding proteins are provided. For example, a biological process can be affected by administering a functional nucleic acid to a cell or a subject, where the functional nucleic acid is selenium-derivatized nucleic acid. As another example, a biological process can be affected by bringing into contact a nuclease and a functional nucleic acid, where the functional nucleic acid is selenium-derivatized nucleic acid.

In some forms of the method, the functional nucleic acid can be an aptamer, an antisense nucleic acid, an siRNA, an shRNA, or a crRNA. In some forms of the method, the functional nucleic acid can bind to or affect a molecule of interest. In some forms, the functional nucleic acid can be a substrate or cofactor for a nuclease. In some forms, the cofactor can be a substrate-guiding sequence (or guide), which directs a nuclease to cleave a substrate (an RNA or DNA). In some forms, catalytic activity of the nuclease is increased in the presence of the selenium-derivatized nucleic acid compared to catalytic activity of the nuclease in the presence of a corresponding nucleic acid that is not selenium-derivatized. For example, the comparison catalytic activity can be the catalytic activity of the nuclease in the presence of the corresponding native nucleic acid. The nuclease can be any type or form of nuclease. Thus, the disclosed selenium-derivatized nucleic acids can be used to affect or alter activity of a nuclease, such as by increasing catalytic activity of the nuclease. In the case of functional nucleic acids, such as siRNA, shRNA, miRNA, crRNA, tracrRNA, and guide sequences, the selenium-derivatized forms can affect or alter the nucleic acid regulation, editing, etc., of the functional nucleic acids.

The nuclease can be any type or form of nuclease. For example, the nuclease can be an endonuclease, an exonuclease, a ribonuclease, a deoxyribonuclease, a ribozyme, a transcription activator-like effector nuclease (TALEN), a Zinc finger nuclease, an RNA-induced silencing complexes (RISC), an Argonaute, a Dicer, a CRISPR-associated (Cas) nuclease, a restriction enzyme, a meganuclease, an RNase A, an RNase H, an RNase I, an RNase III, an RNase L, an RNase P, an RNase T1, an RNase T2, an RNase U2, an RNase V, an RNase V1, an RNase PhyM, an RNase II, an RNase R, an RNase PH, an RNase D, an RNase T, a polynucleotide phosphorylase (RNPase), an oligoribonuclease, an exoribonuclease I, an exoribonuclease II, a micrococcal nuclease, an S1 nuclease, a P1 nuclease, a peptidyl transferase 23S rRNA, a Group I intron, a Group II intron, a GIR1 branching enzyme, a leadzyme, a hairpin ribozyme, a twister ribozyme, a hammerhead ribozyme, an HDV ribozyme, a mammalian CPEB3 ribozyme, a VS ribozyme, a glmS ribozyme, or a CoTC ribozyme. Combinations of nucleases can be targeted. Combinations of nucleases can be guided with selenium-derivatized nucleic acids.

EXAMPLES

Materials and Methods

A. Oligonucleotide and Protein Preparation and Crystallization.

The native and modified DNA or RNA oligonucleotides synthesized in the laboratory (Salon et al., Nucleic Acids Res., 36:7009-7018 (2008)) were purified by HPLC twice with and without DMTr-protection group in order to guarantee high purity. Protein expression (Nowotny et al., Cell, 121:1005-1016 (2005); Nowotny and Yang, Embo J., 25:1924-1933 (2006)) was carried out in BL21 (DE3; pLys E. coli; purchased from Invitrogen). Transformation was accomplished by the heat shock method. The DNA portion of the DNA/RNA duplex (5'-ATGTCGp-3'/5'-UCGACA-3'; one-base overhang at both ends) was derivatized. Prior to co-crystallization with RNase H, the purified Se-DNA (5'-AT-$^{Se}$G-TC-$^{Se}$Gp-3') and RNA (5'-UCGACA-3') were annealed at 1:1 molar ratio by heating the mixture to 90° C. for 1 min, and then allowing it to cool slowly down to 25° C. The resulting Se-DNA/RNA duplex was mixed with the protein (final concentration: 8 mg/mL) at 1:1 molar ratio in the presence of 5 mM MgCl$_2$. Co-crystallization of Se-DNA/RNA duplex with RNase H was achieved by screening with the QIAGEN Classics Suite Kit (www.qiagen.com). By using the sitting-drop vapor diffusion method at 25° C., the crystals were readily obtained from a mixture of the crystallization screen [Buffer: 0.1 M MES, pH 6.5; precipitant: 12% (w/v), PEG 20000].

B. MAD Data Collection, Phasing, and Structure Determination.

Crystal diffraction data of the Se-DNA/RNA/RNase H complex were collected at beamline X25 and X29 in the National Synchrotron Light Source (NSLS) of the Brookhaven National Laboratory. A number of crystals were scanned to find the ones with strong anomalous scattering at the K-edge absorption of selenium. 25% glycerol was used as a cryoprotectant, while X-ray data were collected under liquid nitrogen stream at 99° K. Each crystal was exposed for 15 seconds per image with one degree rotation, and a total of 180 images were taken for each data set. Two crystals were used to collect the MAD/SAD data sets. All data were processed using HKL2000 and DENZO/SCALEPACK (Otwinowski and Minor, Meth. Enzymol., 276:307-326 (1997)). The structure was solved by the MAD method using the program Solve/Resolve (Terwilliger, Meth. Enzymol., 374:22-37 (2003); Wang et al., Acta Crystallogr. D. Biol. Crystallogr., 60:1244-1253 (2004)). The resulting model was refined using Refmac5 within CCP4i. The DNA/RNA duplex was modeled into the structure using Coot. Metal ions and water molecules were added either automatically or manually using Coot.

C. Catalytic Hydrolysis by RNase H.

The DNA with its complementary RNA was allowed to form a duplex by heating and subsequent cooling. Each RNase H hydrolysis reaction (volume 5 μL) contained DNA template (150 nM final concentration; DNA-N, DNA-S, or DNA-Se) and $^{32}$P-labeled RNA substrate (mixture of cold and hot RNAs; 150 nM final concentration). To each hydrolysis reaction, WT or TR RNase H enzyme (10 nM, final) and the reaction buffer (final conditions: 75 mM KCl, 50 mM Tris-HCl, pH 7.8, 3 mM MgCl$_2$, and 1 mM diborane) were added. The reactions were incubated at 37° C. for 30 min, unless otherwise mentioned.

Example 1: Crystallization, Se-Anomalous Phasing, and Structure Determination of the Se-DNA/RNA/RNase H Complex We have synthesized Se-modified DNAs to investigate the DNA/RNA/RNase H complex. The duplexes of the native and Se-modified oligonucleotides (Salon et al., Nucleic Acids Res., 36:7009-7018 (2008)) were complexed with RNase H (an inactive mutant with a single D132N mutation). The complex of RNase H/RNA/Se-DNA (5'-UCGACA-3'/5'-AT-$^{Se}$G-TC-$^{Se}$Gp-3') was crystallized in a buffer containing 0.1 M MES (pH 6.5) and precipitant (12% w/v, PEG 20000). The crystals were also grown using the sitting drop vapor diffusion method. The crystals appeared within a week and reached their maximum size within a month. Two crystals were used to collect the MAD/SAD data sets. The figure of merit of the individual SAD phasing data was relatively low, which could not produce a good electron density map for the model. One SAD data set was used as a reference for the MAD phasing of the other diffraction data set. The overall figures of merit (FOM) of the initial phases were 0.630, which produced an interpretable electron density map. Anomalous diffraction data from the protein complex crystals containing the Se-oligonucleotides can be collected at the selenium K-edge. After the SAD or MAD dataset is collected from a single crystal, the selenium atoms can be located by direct methods and the phase can be determined similarly to the well-established protein strategy (Elkayam et al., Cell, 150:100-110 (2012); Ferre-D'Amare et al., Nature, 395:567-574 (1998); Hendrickson, Science, 254:51-58 (1991); Hendrickson, Trends Biochem. Sci., 25:637-643 (2000); Schirle and MacRae, Science, 336:1037-1040 (2012); Yang et al., Science 249: 1398-1405 (1990)).

Figure 1C:
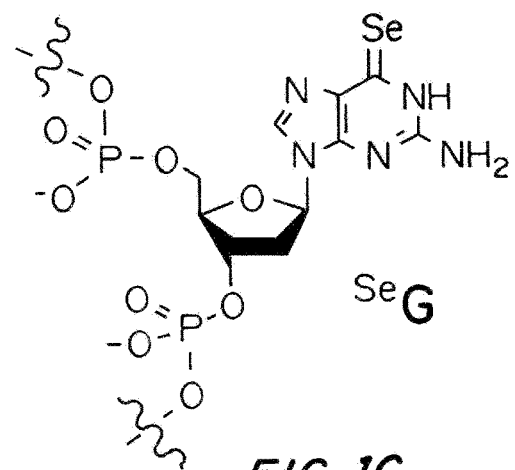

The Se-complex structure was finally determined (3TWH; 1.80 Å resolution; FIG. 1) via the selenium anomalous signal and MAD phasing. Since the inactive mutant enzyme was used, the RNA substrate was not cleaved during the crystallization, which was confirmed by the MS analysis of the crystals. Moreover, the Se-complex structure has been determined by both MAD phasing and molecular replacement. The Se-complex structure determined by the MAD phasing technique is identical to the same complex structure determined by molecular replacement. Compared to the corresponding native structure (2G8U with 2.70 Å resolution) with the same sequences, the Se-containing structure has higher structure resolution.

Figure 2A:
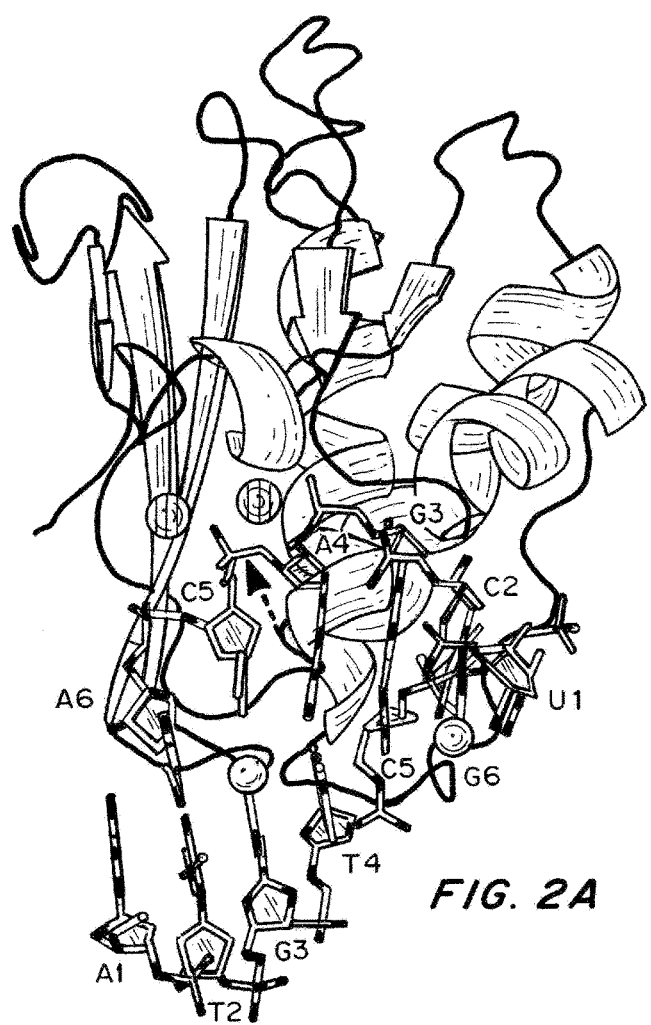
FIGS. 2A and 2B show the structures of RNase H (D132N mutant) complexed with the DNA/RNA duplexes (with the same sequences). (A) The Se-DNA/RNA/RNase H structure (PDB ID: 3TWH; 1.80 Å resolution, from this work). The cleavage site in the Se-structure (3TWH) is between these two $Mg^{2+}$ ions, indicated by the arrow. An RNA strand is shown in ball and stick format in the center of the drawing overlapping with the protein structure. A DNA strand is shown in ball and stick format at the bottom. (B) The native DNA/RNA/RNase H structure (PDB ID: 2G8U; 2.70 Å resolution) (Nowotny and Yang, 2006). The sequences of DNA (5'-ATGTCG-3') and RNA (5'-UCGACA-3') are the same in all structures. An RNA strand is shown in ball and stick format overlapping with the protein and protruding to the bottom right of the drawing. A DNA strand is shown in ball and stick format overlapping with the RNA structure and protruding to the bottom left of the drawing. In both structures, proteins are shown as ribbon diagrams. The spheres represent $Mg^{2+}$ ions and Se atoms, as indicated.
Figure 2B:
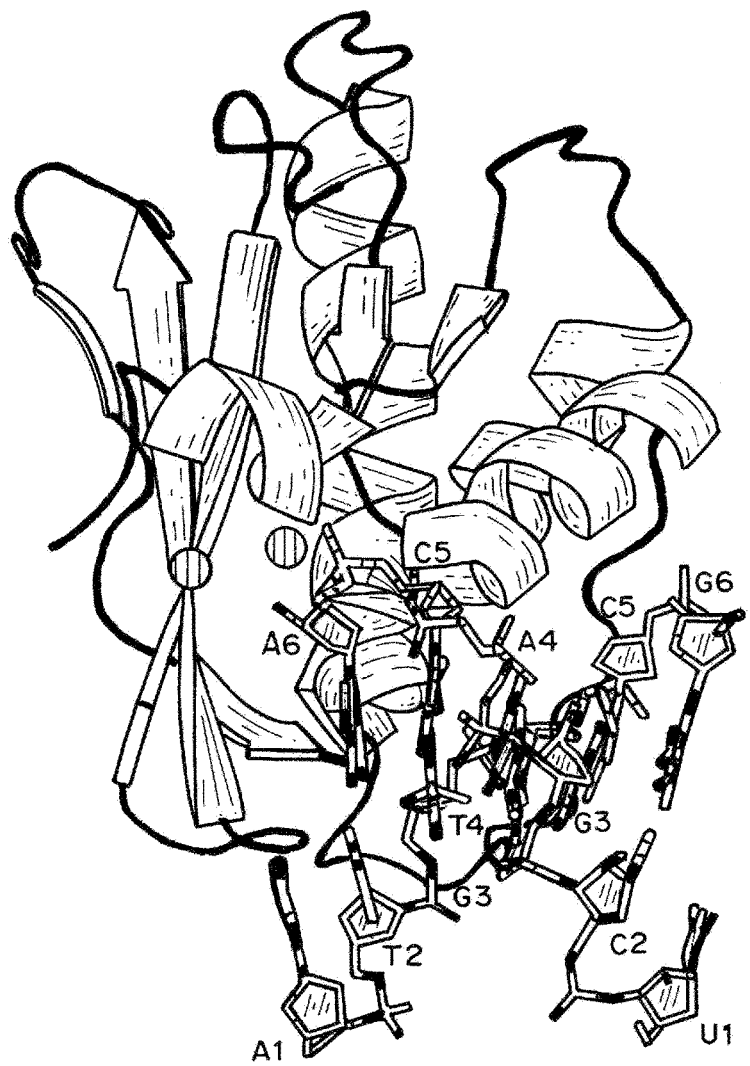

Example 2: Subtle Conformation Change of the RNA/DNA Substrate Duplex by the Selenium Atom on the Nucleobase By taking advantage of selenium atom-specific replacement on the nucleobases (Hassan et al., J. Am. Chem. Soc., 132:2120-2121 (2010); Lin et al., Chem. Soc. Rev., 40:4591-4602 (2011); Salon et al., Nucleic Acids Res., 36:7009-7018 (2008); Salon et al., J. Am. Chem. Soc., 129:4862-4863 (2007); Sheng et al., Nucleic Acids Res., 40:8111-8118 (2012); Sun et al., Nucleic Acids Res., 40:5171-5179 (2012); Zhang et al., Chem. Asian J., 7:476-479 (2012)), the impact of the RNA/DNA duplex and conformation change on the catalytic hydrolysis was investigated. The crystal structure (FIG. 1) of *Bacillus halodurans* RNase H complexed with RNA/DNA modified at the guanosine of position 6 with selenium was determined at 1.80 Å resolution. RNase H is a sequence-non-specific enzyme, and its binding of RNA at different locations is possible. Except for RNase H binding to the Se-modified duplex by a two-nucleotide shift with respect to the native duplex, the Se-derivatized complex structure is virtually identical to the corresponding native complex structure with the same RNA/DNA sequence (FIG. 2) (Nowotny et al., Embo J., 27:1172-1181 (2008); Nowotny et al., Cell, 121: 1005-1016 (2005)). The active site of RNase H is positioned at the phosphate linkage between A4 and C5 of the RNA molecule in the Se-modified duplex, where C5 pairs with $^{Se}$G3 of the DNA sequence (FIGS. 1A and 1B). The C5 5'-phosphate apparently is the scissile phosphate. On the contrary, the active site of RNase H complexed with the corresponding native RNA/DNA duplex (PDB ID: 2G8V and 2G8U) (Nowotny et al., Cell, 121:1005-1016 (2005); Nowotny and Yang, Embo J., 25:1924-1933 (2006)) is positioned at the interface between A6 and U1 in two different RNA molecules in the pseudofiber formed via the stacking of the multiple RNA/DNA duplexes.

Figure 3A:
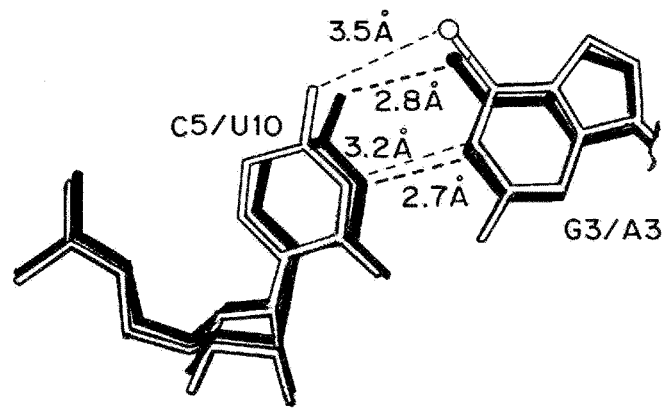
FIGS. 3A, 3B, and 3C show the subtle conformational change (or local subtle unwinding) of the Se-DNA/RNA duplex complexed with RNase H. (A) Local subtle unwinding of the duplex shown via comparison of Se-dG3/rC5 base pair (in 3TWH) with dA3/rU10 (in 1ZBI) at the active site of RNase H. (B) Structural comparison showing the local backbone shift. The structures are shown in the same orientation as in FIG. 3A. The rA/T base pairs (labeled as A4/A9 pairing with T4/T4) next to the scissile phosphate in both structures (1ZBI and 3TWH) are virtually identical. (C) The electron density map of the $C/^{Se}G$ base pair (rC5/dG3); 2Fo-Fc map is contoured at the 1.5 σ level.
Figure 3B:
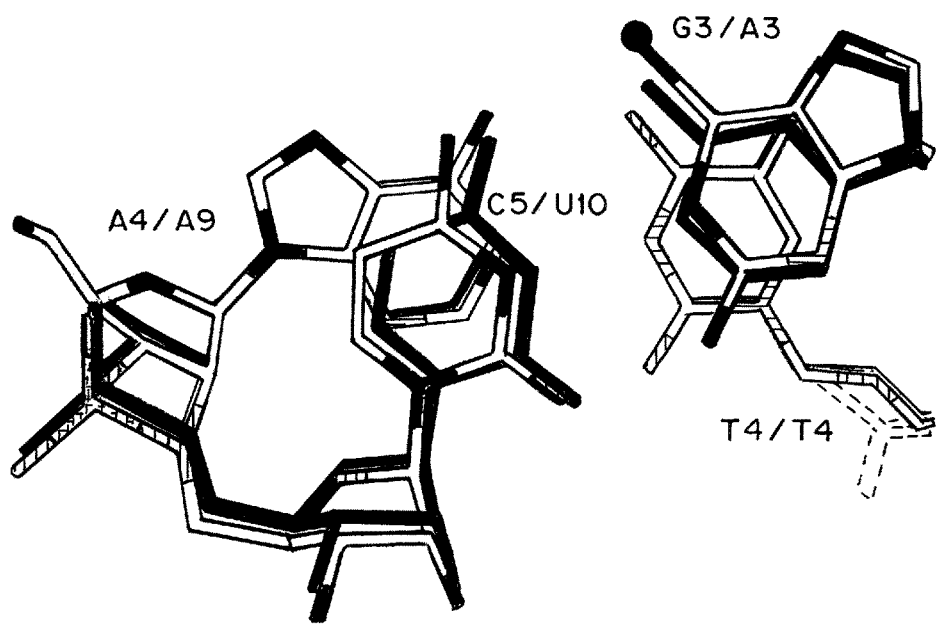
Figure 3C:
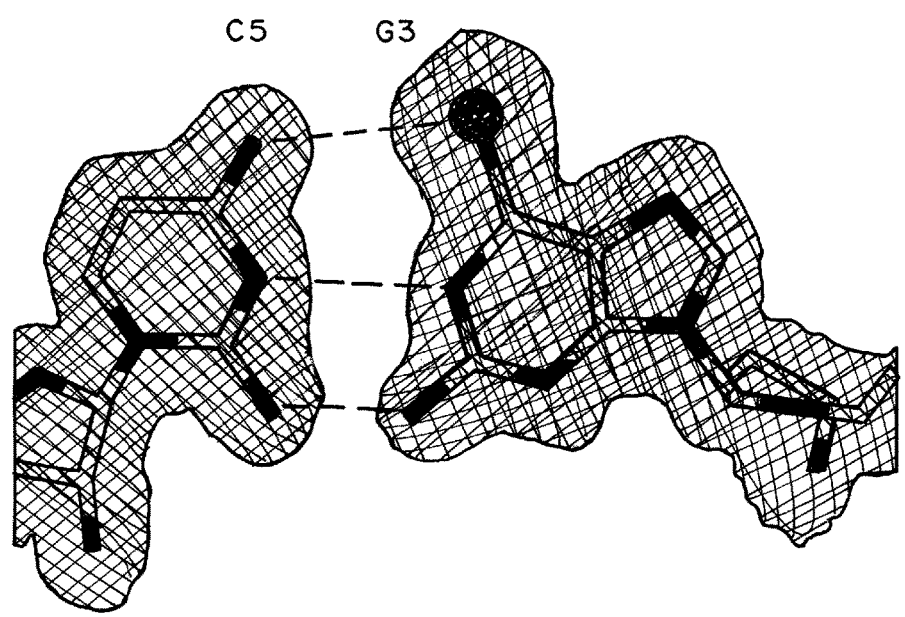

The crystal structure indicated that the Se-modified short RNA/DNA duplex (3'-ACAGCU-5'/5'-AT-$^{Se}$G-TC-$^{Se}$Gp-3') resulted in formation of the substrate-RNase H complex (FIGS. 1A and 2A), instead of the product-RNase H complex originally designed and formed by the corresponding native RNA/DNA substrate duplex (2G8V and 2G8U). The structure of the substrate-RNase H complex (PDB ID: 1ZBI; 1.85 Å resolution) was determined with a longer RNA/DNA duplex substrate (Nowotny et al., Cell, 121:1005-1016 (2005); Nowotny and Yang, Embo J., 25:1924-1933 (2006)), such as a 12-bp RNA/DNA duplex (5'-GAATCAGGTGTC-3' (SEQ ID NO:1)/3'-CUUAGUCCACAG-5' (SEQ ID NO:2)), where two RNase H molecules were bound. Despite the shift of the RNase H binding site, the Se-DNA/RNA duplex retains a very similar overall structure to the corresponding native one. However, a subtle conformation change (by 0.5-0.7 Å) of the Se-dG3/rC5 base pair has been observed, when comparing the Se-modified substrate-enzyme complex (PDB ID: 3TWH) with the native substrate-RNase H complex (FIG. 3A, PDB ID: 1ZBI). The rA/T base pairs next to the scissile phosphate in these two structures are virtually identical (FIG. 3B).

Example 3: The Substrate Shifts its Scissile Phosphate to the RNase H Active Site The small conformational change by the selenium atom on the nucleobase causes a local subtle unwinding of the DNA/RNA duplex. Consistently, the crystal structure study (FIG. 4) indicated that the subtle unwinding leads to a small shift of the scissile phosphate closer to the RNase H active site. The 5'-phosphate of rC5 (the scissile phosphate) in the Se-modified complex is shifted toward the active center of RNase H by approximately 0.3 Å due to the local subtle unwinding of the DNA/RNA duplex. The Se-DNA/RNA/ RNase H complex (PDB ID: 3TWH) was determined at a high resolution (1.80 Å), and the estimated overall coordinate error is approximately 0.1 Å. This complex (3TWH) is considered as a substrate-enzyme complex (the Se-complex), which is related to another substrate-enzyme complex (the native complex, containing the D132N mutation) determined at a high resolution (PDB ID: 1ZBI; 1.85 Å resolution) (Nowotny et al., Cell, 121:1005-1016 (2005); Nowotny and Yang, Embo J., 25:1924-1933 (2006)). Therefore, comparing these two structures allowed observation of the backbone shift in the Se-complex in respect to the native one. A small change in a substrate structure (such as a fraction of 1 Å) is sufficient for catalysis and can contribute to acceleration of the reaction, which has been observed in the case of isocitrate dehydrogenase catalysis (Mesecar et al., Science, 277:202-206 (1997)).

Figure 4A:
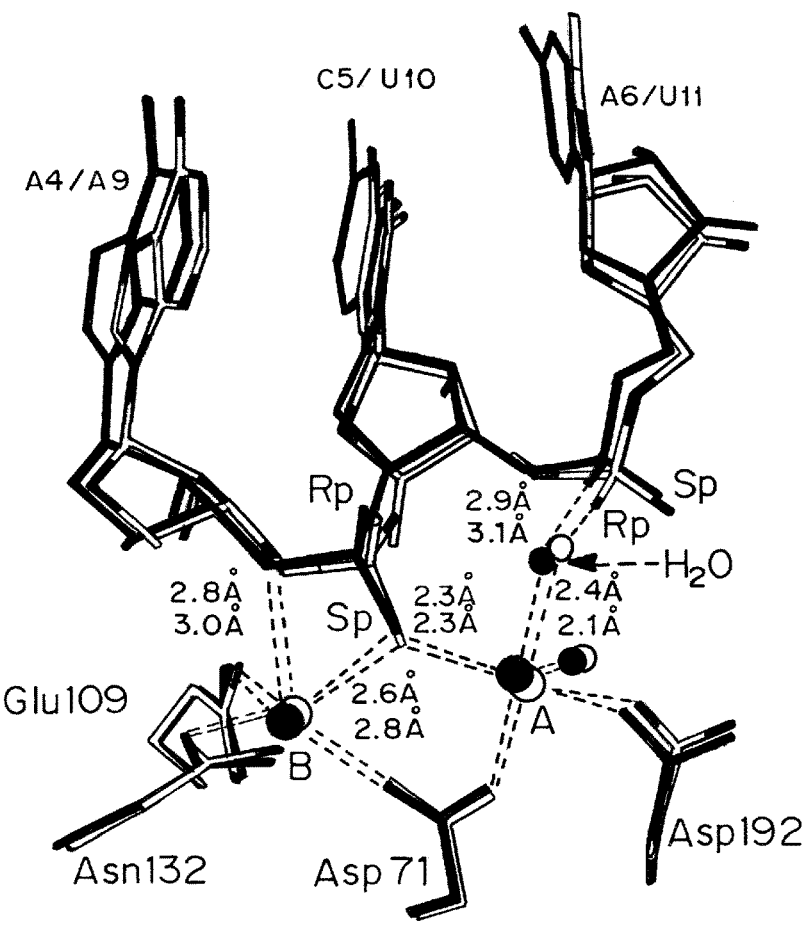
FIGS. 4A and 4B show shift of the scissile phosphate of the Se-DNA/RNA substrate towards the RNase H active site. Water and $Mg^{2+}$ ions are shown as spheres. (A) Superposition of the D132N mutant•Se-DNA/RNA and D132N mutant•DNA/RNA, showing the cleavage site interactions highlighted with the distances. (B) The proposed guide-dependent RNA cleavage facilitated by the scissile phosphate and the local subtle unwinding. The Rp-oxygen atom of the scissile phosphate forms the hydrogen bond with the nucleophilic water molecule. The hydrogen bond values of the Se-modified complex structure are 3.1 Å and 2.9 Å, as shown.

Example 4: The Scissile Phosphate Forms a Hydrogen Bond with the Nucleophilic Water The distances of $Mg^{2+}$-A to the pro-Sp oxygen of the scissile phosphate remain the same (2.3 Å) in both the native and Se-modified structures (FIG. 4A). In contrast, the distances of $Mg^{2+}$-B to the pro-Sp and 3' oxygen atoms of the scissile phosphate (2.6 and 2.8 Å, respectively) are shortened by 0.2 Å in the Se-modified structure, compared with those in the native complex (FIG. 4A). The shortened distances between $Mg^{2+}$-B and these two oxygen atoms indicate their stronger interactions, which is consistent with the catalyzed RNA cleavage. The changes in the distances are also consistent with the B-factors of $Mg^{2+}$-B, which are higher than the B-factors of $Mg^{2+}$-A in both the native and Se-modified structures. This indicates that $Mg^{2+}$-B is more dynamic than $Mg^{2+}$-A in both structure and catalysis.

Figure 4B:
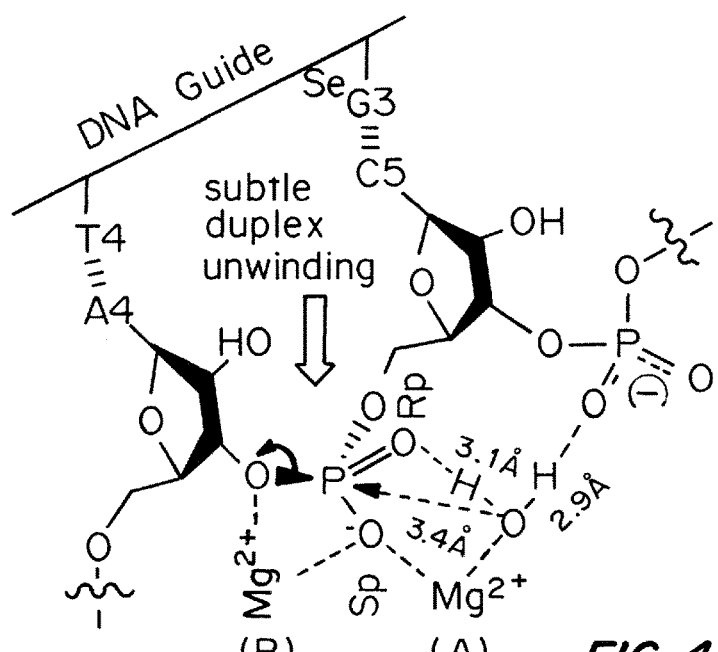

Similarly, the hydrogen bond (2.9 Å in length) between the nucleophilic water and the pro-Rp oxygen of the 3'-phosphate next to the scissile phosphate is stronger and shorter (by 0.2 Å), compared to that in the native system. On the contrary, the distance between this nucleophilic water molecule and $Mg^{2+}$-A (2.4 Å) is longer by 0.3 Å. Weakening the nucleophile bonding with $Mg^{2+}$-A and strengthening the H-bond with the deprotonating pro-Rp oxygen of the 3'-phosphate next to the scissile phosphate are consistent with the "in-line" attack of the nucleophilic water on the scissile phosphorous center (FIG. 4). The nucleophilic water molecule is in close proximity (3.4 Å) to the scissile phosphorous center. Interestingly, this nucleophilic water molecule is also close to the pro-Rp oxygen of the scissile phosphate (3.10 Å), and they form a genuine hydrogen bond. This H-bond can help position the nucleophilic water molecule in the structure.

Example 5: RNA/DNA Minimal Substrates for RNase H Catalytic Cleavage

Unlike the native substrate-enzyme complex using a 12-bp RNA/DNA duplex (PDB ID: 1ZBI), where RNase H can bind more than one site, the short Se-DNA/RNA substrate (with 5 base pairs; FIG. 1) allows only one RNase H molecule to bind, due to its minimal size. Interestingly, this duplex substrate with a small size forces RNase H to interact with the RNA/DNA duplex in a "pseudo-specific" manner. On the basis of the crystal structure, it was predicted that RNase H cleaved the RNA substrate at 5'-phosphate of C5 and only offered two fragments, i.e., the 5'-product (5'-UCGA-3') and the 3'-product (5'-pCA-3'). This was confirmed by RNA substrate digestion. RNase H generated one 5'-product (Figure SA), and the radioactive intensity of the cleaved product was equal to the intensity of the starting material.

On the basis of the crystal structure (FIG. 4), it was also predicted that a sulfur-modification at C5 5'-phosphate (such as sulfur replacement of a non-bridging oxygen atom) can significantly inhibit the RNA cleavage. As expected, the S-modifications of C5 5'-phosphate (replacing the pro-Sp or pro-Rp oxygen atom) indeed prevented the RNA substrate cleavage (FIGS. 5B and 5C). The sulfur substitution of the pro-Sp oxygen of the scissile phosphate disrupts the interaction with both $Mg^{2+}$ ions (FIG. 5B), while the sulfur replacement of the pro-Rp oxygen of the scissile phosphate disrupts the interaction between the scissile phosphate and the nucleophilic water molecule. Therefore, both sulfur modifications inhibit the RNA cleavage (FIGS. 5B and 5C).

Notably, the compensation experiment by switching from $Mg^{2+}$ to $Mn^{2+}$ cation can effectively recover the cleavage of the Sp-modified RNA (FIG. 5D) due to re-establishment of the interactions between the cations ($Mn^{2+}$) and the Sp-sulfur atom (FIGS. 4 and 5D). These results confirm the crystal structure conclusion: the C5 5'-phosphate is indeed the cleavage site. This minimal substrate opens up the opportunity for atom-specific substitution and kinetic studies to address the impact of the duplex conformation on the guide-dependent RNA cleavage. The experimental results of the RNA sulfur-modifications have demonstrated that both pro-Sp and pro-Rp oxygen atoms of the scissile phosphate play critical roles in the RNA cleavage, which is consistent with the computation study and prediction (De Vivo et al., J. Am. Chem. Soc., 130:10955-10962 (2008); Elsasser and Fels, Phys. Chem. Chem. Phys. 12:11081-11088 (2010); Rosta et al., J. Am. Chem. Soc., 133:8934-8941 (2011)).

RNase H is a sequence-non-specific endonuclease that selectively digests the RNA portion of RNA/DNA duplexes (Stein and Hausen, Science, 166:393-395 (1969)). RNase H is involved in many important biological processes (Arnold et al., Nature, 357:85-89 (1992); Green et al., Cold Spring Harb. Symp. Quant. Biol., 39:975-985 (1975); Hippenmeyer and Grandgenett, J. Biol. Chem., 260:8250-8256 (1985); Wintersberger, Pharmacol. Ther., 48:259-280 (1990)), including removal of the RNA primers from Okazaki fragments in replication. It can also silence gene expression directly via the antisense mechanism (Veal et al., Nucleic Acids Res., 26:5670-5675 (1998); Vickers et al., J. Biol. Chem., 278:7108-7118 (2003); Walder and Walder, Proc. Natl. Acad. Sci. USA, 85:5011-5015 (1988); Wu et al., J. Biol. Chem., 279:17181-17189 (2004)). Catalytic studies on RNase H have been performed extensively, especially investigating the roles of the metal cations near the scissile phosphate. Recently the crystal structures of Bacillus halodurans RNase H and human RNase H1 complexed with RNA/DNA duplex substrates were determined at 1.5 and 2.2 Å resolution, respectively. These structures provide insights into cation-assisted RNA hydrolysis (Nowotny et al., Mol. Cell, 28:264-276 (2007); Yang et al., Mol. Cell, 22:5-13 (2006)).

The complex structure of RNase H/RNA/Se-DNA, which was determined via the Se-nucleic acid MAD phasing is described. The RNase H/RNA/DNA complex was used as a model system to demonstrate the proof of principle of crystal structure determination using Se-derivatized nucleic acids instead of proteins. The RNA cleavage by RNase H is facilitated by a local subtle unwinding of the DNA/RNA duplex, thereby shifting the RNA scissile phosphate closer to the enzyme active site. Moreover, it was experimentally observed that in the presence of RNase H, the scissile phosphate formed a hydrogen bond with the water nucleophile, thus helping to position the water molecule in the structure.

Example 6: The Se-Modified DNA Accelerates RNA Substrate Hydrolysis Catalyzed by RNase H On the basis of the structure study, it was hypothesized that due to the facilitated subtle change in conformation (or local subtle unwinding of the DNA/RNA duplex), the Se-DNA guide can better assist RNase H in catalyzing RNA hydrolysis than the corresponding native DNA guide. Thus, RNA hydrolysis was carried out by RNase H in the presence of the native and S- and Se-nucleobase-modified DNAs (FIGS. 1B and 5E). The relative reaction rates in the presence of the native (DNA-N) and modified DNAs were measured. Consistent with this hypothesis, the Se-DNA guide (DNA-Se) in the RNA cleavage is much more efficient (6.2 fold faster) than the corresponding native DNA, while the S-DNA (DNA-S) is 1.6-fold more efficient than the native form. The experimental results indicate that the subtle conformation change via the single-atom nucleobase modification can push the scissile phosphate towards the enzyme active site, thereby significantly accelerating the RNA cleavage.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for crystallographic analysis of a molecule of interest, comprising the steps of
   (a) contacting the molecule of interest with selenium-derivatized nucleic acid to form a molecule of interest/selenium-derivatized nucleic acid complex, wherein the selenium-derivatized nucleic acid comprises a selenium at the 6-position of guanosine;
   (b) crystallizing the molecule of interest/selenium-derivatized nucleic acid complex, and
   (c) determining the X-ray crystal structure of the molecule of interest/selenium-derivatized nucleic acid complex, wherein the X-ray crystal structural determination comprises single-wavelength anomalous diffraction (SAD) phasing of the selenium-derivatized nucleic acid.

2. The method of claim 1, wherein the resolution of diffraction of the X-ray crystallographic data obtained with the selenium-derivatized nucleic acid complex is greater than that of crystallographic data obtained in the absence of selenium-derivatized nucleic acid.

3. The method of claim 1, wherein the molecule of interest does not crystallize in the absence of selenium-derivatized nucleic acid.

4. The method of claim 1, wherein phases for the X-ray crystal structure of the molecule of interest are not provided from another crystal.

5. The method of claim 1, wherein the molecule of interest is a polypeptide.

6. The method of claim 1, wherein the molecule of interest is not a nucleic acid-binding protein.

7. The method of claim 1, further comprising identifying the interfacing elements between the molecule of interest and selenium-derivatized nucleic acid in the three dimensional X-ray crystal structure of the molecule of interest/selenium-derivatized nucleic acid complex.

8. The method of claim 7, further comprising selecting a candidate molecule that interferes with the interaction between the molecule of interest and the nucleic acid, wherein the candidate molecule is selected by
   (a) providing on a digital computer the three-dimensional X-ray crystal structure of the molecule of interest/selenium-derivatized nucleic acid complex; and
   (b) selecting a candidate molecule predicted to bind the nucleic acid interface identified in the polypeptide/selenium-derivatized nucleic acid complex structure.

9. The method of claim 7, further comprising designing a candidate molecule that binds to the molecule of interest, wherein the candidate molecule is designed by
   (a) providing on a digital computer the three-dimensional crystal structure of the molecule of interest/selenium-derivatized nucleic acid complex; and
   (b) using software comprised by the digital computer to design a candidate molecule that is predicted to bind to the polypeptide.

10. The method of claim 9, further comprising
    (a) synthesizing the candidate molecule; and
    (b) evaluating the candidate molecule for an ability to alter an activity of the molecule of interest.

11. The method of claim 10, wherein the molecule of interest is a polypeptide.

12. The method of claim 1, wherein the selenium-derivatized nucleic acid is selenium-derivatized RNA.

13. The method of claim 1, wherein the selenium-derivatized nucleic acid binds to the molecule of interest with at least the same affinity as nucleic acid that is not selenium-derivatized.

14. The method of claim 1, wherein the selenium-derivatized nucleic acid binds the same region of the molecule of interest as nucleic acid that is not selenium-derivatized.

* * * * *

SEQUENCE LISTING

<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Forms 12-bp RNA/DNA duplex with SEQ ID NO:2

<400> SEQUENCE: 1
gaatcaggtg tc                                                                12

<210> SEQ ID NO 2
<211> LENGTH: 12
<212> TYPE: RNA
<213> ORGANISM: Artificial Sequence
<220> FEATURE:
<223> OTHER INFORMATION: Forms 12-bp RNA/DNA duplex with SEQ ID NO:1

<400> SEQUENCE: 2
gacaccugau uc                                                                12